US012778562B2

(12) United States Patent
Nishiura et al.

(10) Patent No.: US 12,778,562 B2
(45) Date of Patent: Nov. 3, 2026

(54) ULTRASOUND PHANTOM AND METHOD OF PRODUCING ULTRASOUND PHANTOM

(71) Applicant: CANON KABUSHIKI KAISHA, Tokyo (JP)

(72) Inventors: Chiaki Nishiura, Tokyo (JP); Ryo Ogawa, Kanagawa (JP); Kyohei Wada, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 324 days.

(21) Appl. No.: 18/596,812

(22) Filed: Mar. 6, 2024

(65) Prior Publication Data

US 2024/0299014 A1 Sep. 12, 2024

(30) Foreign Application Priority Data

Mar. 9, 2023 (JP) ................................ 2023-036754
Jan. 25, 2024 (JP) ................................ 2024-009744

(51) Int. Cl.
*A61B 8/00* (2006.01)

(52) U.S. Cl.
CPC .................................. *A61B 8/587* (2013.01)

(58) Field of Classification Search
CPC ................................................ A61B 8/587
See application file for complete search history.

(56) References Cited

U.S. PATENT DOCUMENTS 4,277,367 A * 7/1981 Madsen ................. G01N 29/30
73/600
4,647,470 A * 3/1987 Sanderson ............ A23L 13/422
426/573
4,894,013 A * 1/1990 Smith .................... A61B 8/587
434/268
5,061,187 A * 10/1991 Jerath .................. G09B 23/286
434/273
6,238,343 B1 * 5/2001 Madsen ................. G01N 29/30
600/437
9,452,135 B2 * 9/2016 Jacobs ................. A61K 31/137
11,176,848 B1 * 11/2021 Chen ...................... A61B 8/587
2015/0140113 A1 * 5/2015 Jacobs .................. A23L 29/269
514/630
2023/0097162 A1 3/2023 Wada et al.
2024/0307039 A1 * 9/2024 Wada ..................... A61B 8/587

FOREIGN PATENT DOCUMENTS

JP 2002-360572 A 12/2002
JP 2004105031 A * 4/2004 ............. A23L 21/10

OTHER PUBLICATIONS

Wada et al., U.S. Appl. No. 18/598,091, filed Mar. 7, 2024.

* cited by examiner

*Primary Examiner* — Jonathan M Dunlap
(74) *Attorney, Agent, or Firm* — VENABLE LLP

(57) ABSTRACT

Provided is an ultrasound phantom including a hydrogel, wherein the hydrogel contains water, a first polysaccharide containing a glucose residue in a main chain thereof, and a mannose residue and a glucuronic acid residue in a side chain thereof, and a second polysaccharide containing a mannose residue in a main chain thereof and a galactose residue in a side chain thereof, and wherein the hydrogel has a Young's modulus of 0.1 kPa or more and 5.0 kPa or less.

13 Claims, 2 Drawing Sheets

ULTRASOUND PHANTOM AND METHOD OF PRODUCING ULTRASOUND PHANTOM

BACKGROUND OF THE DISCLOSURE

Field of the Disclosure

The present disclosure relates to an ultrasound phantom and a method of producing an ultrasound phantom.

Description of the Related Art

A medical image diagnostic apparatus, such as an acoustic wave diagnostic apparatus, a magnetic resonance imaging diagnostic apparatus, an X-ray image diagnostic apparatus, or a near-infrared imaging apparatus, performs diagnosis by: applying a sound wave, an electromagnetic wave, or the like to a site to be observed; and observing the sound wave or the electromagnetic wave that has been reflected or transmitted. A living organism tissue-approximated phantom simulating the reflection and absorption characteristics of a living organism for the sound wave, the electromagnetic wave, or the like has been used for calibrating the above-mentioned image diagnostic apparatus and enlarging its measurement range.

An ultrasonic diagnostic apparatus is a diagnostic apparatus that can observe the reflected wave of an ultrasonic wave from a site to be observed to image the state of the inside of the site. Further, an evaluation method called a shear wave elastography method by which the Young's modulus of the site to be observed can be quantified has also been known. One specific method is a method including exciting the site to be observed to measure the propagation velocity distribution of a generated shear wave, to thereby image the distribution of the Young's moduli.

Meanwhile, to obtain a satisfactory image, the site to be observed and the probe of a measuring apparatus need to be brought into close contact with each other. Accordingly, as the site to be observed deforms to a larger extent, the pressing of the measuring probe against the site occurs more frequently.

In Japanese Patent Application Laid-Open No. 2002-360572, there is a disclosure of a living organism-simulated phantom including: a thermally reversible hydrogel obtained by mixing glucomannan serving as a main component and a polysaccharide gum serving as a residual component; and a thermally irreversible hydrogel produced by mixing glucomannan and an alkaline component. The living organism-simulated phantom has high mechanical strength, has an elastic force, and has high tear strength. Accordingly, the phantom has a feature in that the phantom does not easily break, and hence the phantom is not only used for calibrating an ultrasonic diagnostic apparatus but also can be repeatedly used in the insertion of a needle or the like for the acquisition of an operation technique.

In general, a hydrogel including water and a polysaccharide is particularly suitable as a living organism-simulated material for an ultrasonic diagnostic apparatus because the velocity of a sound passing therethrough is close to that in a living organism, and hence the acoustic attenuation thereof is low. However, the hydrogel using the polysaccharide has a characteristic in that the hydrogel does not gelate unless the hydrogel contains a certain concentration or more of the polysaccharide, and hence its Young's modulus in a low concentration region is difficult to control. In addition, the hydrogel has the following drawback: depending on the kind of the polysaccharide, the breakage of the gel is easily caused by a low compressive strain, and hence the hydrogel cannot resist repeated use.

No specific measured data on the ease with which the hydrogel disclosed in Japanese Patent Application Laid-Open No. 2002-360572, the hydrogel containing glucomannan as a main component, breaks has been disclosed. In addition, no specific measured data on the Young's modulus of the hydrogel has been similarly disclosed.

SUMMARY OF THE DISCLOSURE

An ultrasound phantom according to one embodiment of the present invention is an ultrasound phantom including a hydrogel, wherein the hydrogel contains water, a first polysaccharide containing a glucose residue in a main chain thereof, and a mannose residue and a glucuronic acid residue in a side chain thereof, and a second polysaccharide containing a mannose residue in a main chain thereof and a galactose residue in a side chain thereof, and wherein the hydrogel has a Young's modulus of 0.1 kPa or more and 5.0 kPa or less.

Further features of the present disclosure will become apparent from the following description of exemplary embodiments with reference to the attached drawings.

DESCRIPTION OF THE EMBODIMENTS

Figure 1:
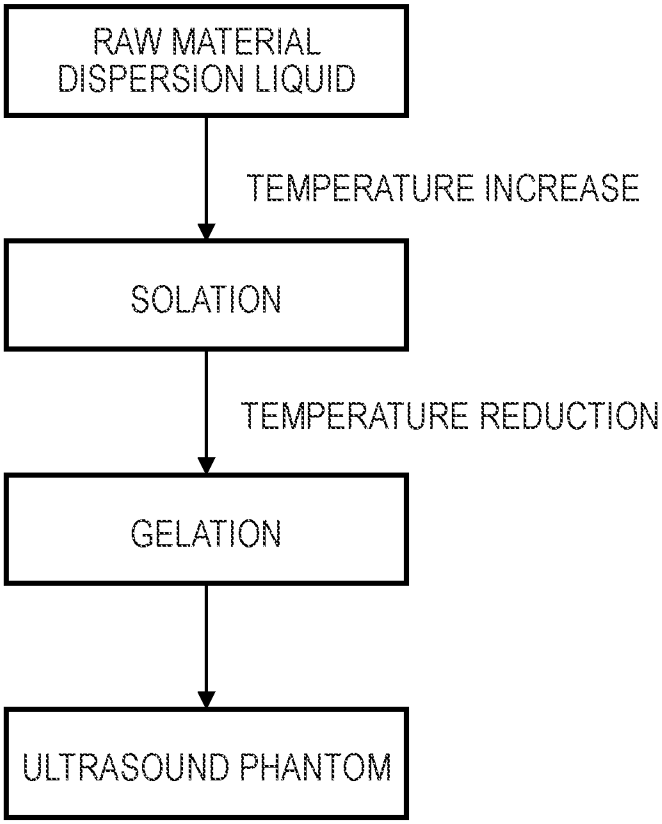
FIG. 1 is a flowchart for illustrating an example of a method of producing an ultrasound phantom of the present disclosure.

In the present disclosure, the description "XX or more and YY or less" or "XX to YY" representing a numerical range means a numerical range including a lower limit and an upper limit that are end points unless otherwise stated. When the numerical ranges are described in stages, the upper and lower limits of each numerical range may be arbitrarily combined.

An ultrasound phantom according to this embodiment is an ultrasound phantom including a hydrogel, wherein the hydrogel contains water, a first polysaccharide containing a glucose residue in a main chain thereof, and a mannose residue and a glucuronic acid residue in a side chain thereof, and a second polysaccharide containing a mannose residue in a main chain thereof and a galactose residue in a side chain thereof, and wherein the hydrogel has a Young's modulus of 0.1 kPa or more and 5.0 kPa or less.

The materials to be incorporated into the hydrogel for forming the ultrasound phantom according to this embodiment, the configuration of the phantom, and the like are described below.

<Polysaccharides>

The polysaccharides in this embodiment each have a structure in which many monosaccharide molecules are linked to each other. A glycosidic bond is preferred as a bond through which the monosaccharide molecules are linked to each other from the viewpoint of ease of availability. A monosaccharide molecule structure after bonding through the glycosidic bond is hereinafter referred to as "sugar residue."

The conformation of a sugar residue may be any one of a D-form and an L-form, or may be a mixture thereof. When the sugar residue has a ring structure, the position of a hydroxyl group bonded to anomeric carbon may be any one of a cis-form (α-anomer) and a trans-form (β-anomer), or may be a mixture thereof.

In addition, when the sugar residue has a carboxylic acid, the hydrogen atom of the carboxylic acid may be substituted with a monovalent cation, such as a sodium ion or a potassium ion. Further, the atom may be substituted by the formation of a crosslinked structure between a divalent cation, such as a calcium ion or a magnesium ion, and a neighboring carboxylic acid anion present in a molecule, or between the molecules, of the sugar residue.

<First Polysaccharide>

The first polysaccharide in this embodiment contains the glucose residue in its main chain, and the mannose residue and the glucuronic acid residue in its side chain, and may contain a sugar residue except the sugar residues.

The mass ratio of the glucose residue present in the main chain in the first polysaccharide is preferably 90 mass % or more, more preferably 95 mass % or more, still more preferably 99 mass % or more from the viewpoint of ease of availability.

The glucose residue present in the main chain is preferably a D-glucose residue or a β-glucose residue, more preferably a β-D-glucose residue from the viewpoint of ease of availability.

With regard to the position of a glycosidic bond through which the glucose residues present in the main chain are linked to each other, a structure in which the 1-position of one glucose residue and the 4-position of another glucose residue are linked to each other through the glycosidic bond is preferred from the viewpoint of ease of availability.

The mass ratio of the total of the mannose residue and the glucuronic acid residue present in the side chain in the first polysaccharide is preferably 90 mass % or more, more preferably 95 mass % or more, still more preferably 99 mass % or more from the viewpoint of ease of availability.

The ratio of the number of the mannose residues present in the side chain to the number of the glucose residues present in the main chain is preferably 0.8 or more and 1.2 or less, more preferably 0.9 or more and 1.1 or less, still more preferably 0.95 or more and 1.05 or less from the viewpoint of ease of availability.

The ratio of the number of the glucuronic acid residues present in the side chain to the number of the glucose residues present in the main chain is preferably 0.4 or more and 0.6 or less, more preferably 0.45 or more and 0.55 or less, still more preferably 0.48 or more and 0.52 or less from the viewpoint of ease of availability.

The mannose residue present in the side chain is preferably a residue having a D-mannose residue from the viewpoint of ease of availability. In addition, a hydroxyl group at the 6-position of the residue may be acetylated or modified with a hydrocarbon having bonded thereto a quaternary ammonium salt, or the residue may have a structure in which hydroxyl groups at its 4-position and 6-position are crosslinked to each other by pyruvic acid.

The glucuronic acid residue in the side chain preferably has a D-glucuronic acid residue, and more preferably has a β-D-glucuronic acid residue.

With regard to the position of a glycosidic bond between the mannose residue present in the side chain and the glucose residue present in the main chain, a structure in which the 1-position of the mannose residue and the 3-position of the glucose residue are linked to each other through the glycosidic bond is preferred from the viewpoint of ease of availability.

With regard to the position of a glycosidic bond between the mannose residue present in the side chain and the glucuronic acid residue present in the side chain, a structure in which the 2-position of the mannose residue and the 1-position of the glucuronic acid residue, or the 1-position of the mannose residue and the 4-position of the glucuronic acid residue are linked to each other is preferred from the viewpoint of ease of availability.

The order in which the mannose residue and the glucuronic acid residue present in the side chain are bonded to each other is preferably the following order when viewed from a sugar residue bonded to the main chain from the viewpoint of ease of availability: the mannose residue, the glucuronic acid residue, and the mannose residue. The order is more preferably the following order: an α-D-mannose residue whose 6-position is acetylated, a β-D-glucuronic acid residue, and a β-D-mannose residue whose 4-position and 6-position are crosslinked to each other by pyruvic acid.

The first polysaccharide may be a polysaccharide obtained by: giving a microorganism a sugar as a nutrient; and recovering a polysaccharide produced by fermentation or the like. From the viewpoints of ease of availability and quality stability, a xanthan gum, which is a polysaccharide produced by giving *Xanthomonas campestris* a saccharide such as glucose as a nutrient, and recovering and purifying a polysaccharide secreted to the outside of the cells of the bacterium, is preferred. A polysaccharide except the xanthan gum may also be used as the first polysaccharide as long as the polysaccharide shows the same effect as that of the ultrasound phantom of this embodiment.

<Second Polysaccharide>

The second polysaccharide in this embodiment contains the mannose residue in its main chain and the galactose residue in its side chain, and may contain a sugar residue except the sugar residues.

The mass ratio of the mannose residue present in the main chain is preferably 90 mass % or more, more preferably 95 mass % or more, still more preferably 99 mass % or more from the viewpoint of ease of availability.

The mannose residue in the main chain is preferably a D-mannose residue, more preferably a β-D-mannose residue from the viewpoint of ease of availability.

With regard to the position of a glycosidic bond through which the mannose residues present in the main chain are linked to each other, a structure in which the 1-position of one mannose residue and the 4-position of another mannose residue are linked to each other through the glycosidic bond is preferred from the viewpoint of ease of availability.

The mass ratio of the galactose residue present in the side chain is preferably 90 mass % or more, more preferably 95 mass % or more, still more preferably 99 mass % or more from the viewpoint of ease of availability.

The ratio of the number of the galactose residues present in the side chain to the number of the mannose residues present in the main chain is preferably 0.2 or more and 0.4 or less, more preferably 0.2 or more and 0.3 or less, still more preferably 0.23 or more and 0.27 or less from the viewpoint of ease of availability.

The galactose residue in the side chain preferably has a D-galactose residue, and more preferably has an α-D-galactose residue.

With regard to the position of a glycosidic bond between the galactose residue present in the side chain and the mannose residue present in the main chain, a structure in which the 1-position of the galactose residue and the 6-position of the mannose residue are linked to each other through the glycosidic bond is preferred from the viewpoint of ease of availability.

The second polysaccharide may be a polysaccharide obtained by purifying a product separated from a plant raw material. From the viewpoints of ease of availability and quality stability, a tara gum obtained from the endosperm portion of a leguminous tara seed is preferred, and a locust bean gum obtained from the endosperm portion of a leguminous locust bean seed is more preferred. A polysaccharide except the locust bean gum may also be used as the second polysaccharide as long as the polysaccharide shows the same effect as that of the ultrasound phantom of this embodiment.

The first polysaccharide and the second polysaccharide are each preferably in a powder form from the viewpoint of a dissolution rate.

<Method of Measuring Young's Modulus of Hydrogel>

The Young's modulus of the hydrogel in this embodiment may be measured with a viscoelasticity-measuring apparatus. Specifically, the Young's modulus may be measured with a dynamic viscoelasticity-measuring apparatus of a shear system.

With regard to a condition for dynamic viscoelasticity measurement of a shear system, a measurement frequency is desirably 0.01 Hz or more and 1.00 Hz or less in view of followability between the hydrogel and a measuring jig. In addition, from the viewpoint of a measurement error, a measurement strain is desirably 0.01% or more and 1.00% or less. When the measurement strain is less than 0.01%, the gel cannot be sufficiently moved, and hence the reliability of a measured value is not obtained. In addition, when the measurement strain is more than 1.00%, the measuring jig slides, and hence the reliability of the measured value reduces. The measurement was performed by using a sample produced so as to have a diameter of 25 mm and a height of 6 mm. Parallel plates each having a diameter of 25 mm were used as the measuring jig.

The viscoelasticity-measuring apparatus that may be used is, for example, MCR302 dealt in by Anton Paar Japan K.K.

The Young's modulus (E) was calculated in accordance with the following equation (1) when the square root of the sum of squares of the resultant storage modulus (G') and loss modulus (G") was defined as a shear rigidity (G).

$$E = G \times 3 \qquad \text{Equation (1)}$$

The Poisson's ratio of the hydrogel is assumed to be 0.5. In addition, when the loss modulus (G") of the hydrogel is sufficiently low as compared to its storage modulus (G') (e.g., $G''/G'<0.05$), the storage modulus (G') may be calculated as the shear rigidity (G).

The Young's modulus of the hydrogel in this embodiment is preferably 0.1 kPa or more and 5.0 kPa or less, more preferably 0.1 kPa or more and 2.5 kPa or less, still more preferably 0.3 kPa or more and 1.5 kPa or less, still further more preferably 0.6 kPa or more and 1 kPa or less from the viewpoint of ease of production.

<Method of Measuring Compressive Strain-Stress Curve of Hydrogel>

The compressive strain-stress curve of the hydrogel in this embodiment may be measured with a compression test apparatus.

The compressive strain-stress curve was measured under the condition of a compression speed of 10 mm/min. In addition, the maximum of the compressive strain of the hydrogel was set to 80%. The measurement was performed by using a sample produced so as to have a size measuring 29 mm in diameter by 12.5 mm in height.

The compression test apparatus that may be used is, for example, a universal tester RTF-1250 dealt in by A&D Company, Limited.

A state in which the compressive stress of the hydrogel monotonically increases in the compressive strain range of from 0% or more to 50% or less in the resultant compressive strain-stress curve means that the compressive stress continues to increase when the compressive strain is increased in increments of 0.5%. When the intervals at which the compressive strain is measured are less than 0.5%, measured data closest to 0.5×n ("n" represents an integer of from 0 to 100) is adopted.

<Specification of Water Content>

In the ultrasound phantom of this embodiment, at least part of the water preferably hydrates the first polysaccharide and the second polysaccharide, and the first polysaccharide and the second polysaccharide preferably gelate. In addition, in the ultrasound phantom of this embodiment, the first polysaccharide and the second polysaccharide preferably form a hydrogel with at least part of the water. That is, the ultrasound phantom of this embodiment is preferably in a hydrogel state. A water content in the ultrasound phantom of this embodiment is, for example, preferably 50.00 mass % or more and 99.00 mass % or less, more preferably 70.00 mass % or more and 99.00 mass % or less, still more preferably 80.00 mass % or more and 99.00 mass % or less, still further more preferably 84.00 mass % or more and 94.00 mass % or less.

<Definitions of Sol Point and Gel Point>

The mixture of the first polysaccharide and the second polysaccharide has: the first phase transition point at which an aqueous dispersion liquid of the mixture of the first polysaccharide and the second polysaccharide solates through an increase in temperature thereof; and the second phase transition point at which the aqueous solution that has solated gelates through a reduction in temperature thereof. The aqueous dispersion liquid of the mixture of the first polysaccharide and the second polysaccharide is a product obtained by dispersing the first polysaccharide and the second polysaccharide in water. In addition, the first phase transition point is the temperature (solation temperature) at which the aqueous dispersion liquid of the mixture of the first polysaccharide and the second polysaccharide solates when the temperature of the aqueous dispersion liquid is increased. In addition, the second phase transition point is the temperature at which the aqueous solution that has solated gelates when its temperature is reduced.

The mixture of the first polysaccharide and the second polysaccharide typically has the first phase transition point at which the mixture solates through an increase in temperature thereof, and the second phase transition point at which the mixture gelates through a reduction in temperature thereof. The first phase transition point is preferably the temperature at which when the temperature of an aqueous dispersion liquid, which is obtained by dispersing the mixture of the first polysaccharide and the second polysaccharide at 0.5 mass % in water, is increased from room temperature (25° C.), the mixture of the first polysaccharide and the second polysaccharide is dissolved in the water, and hence the aqueous dispersion liquid solates. In addition, the second phase transition point is preferably the temperature at which when the aqueous solution of the mixture of the first polysaccharide and the second polysaccharide that has solated is left at room temperature to be reduced in temperature, the aqueous solution gelates. In the specification of the present application, an equilibrium state in which a specific component is dissolved in water to provide an aqueous solution is distinguished from an equilibrium state in which the specific component is dispersed in the water to provide a dispersion liquid.

<Method of Analyzing Sol and Gel States>

In the present disclosure, the term "gel" refers to a solid state, and the term "sol" refers to a state having fluidity. Viscoelasticity measurement may be used for judging whether an object is gel or sol. Specifically, the judgment may be performed with a dynamic viscoelasticity-measuring apparatus by the following procedure. In addition, although the dynamic viscoelasticity-measuring apparatus comes in a shear system including applying a stress in a lateral direction, and a compression and tension system including applying a stress in a longitudinal direction, the shear system is adopted.

The value of tan δ obtained by dividing the loss modulus of the object by the storage modulus thereof is calculated. When the value is 1.0 or less, the object can be judged to be gel, and when the value is more than 1.0, the object can be judged to be sol. A frequency of 0.01 Hz or more and 1.00 Hz or less can be adopted as a measurement frequency at this time in view of followability between the gel and a measuring jig. A strain at the time of the measurement is desirably 0.01% or more and 1.00% or less. When the strain is less than 0.01%, the gel cannot be sufficiently moved, and hence the reliability of a measured value is not obtained. In addition, when the strain is more than 1.00%, the measuring jig slides, and hence the reliability of the measured value reduces. The viscoelasticity-measuring apparatus that may be used is, for example, MCR302 dealt in by Anton Paar Japan K.K.

<Gelation Mechanism>

In general, the first polysaccharide is dissolved in water at a temperature equal to or more than room temperature to become sol, and the second polysaccharide is dissolved in water by being heated to 80° C. or more, to thereby become sol. The mixture of the first polysaccharide and the second polysaccharide is a hydrogel material that undergoes a structural transition by being cooled to 60° C. or less, to thereby become gel. In a sol state, the entanglement of polymer chains in the first polysaccharide and the second saccharide is released, and hence the polysaccharides are dissolved in water to liquefy. Meanwhile, at the time of the cooling of the mixture, the double-helix structure of the first polysaccharide and the region of the second polysaccharide free of any galactose side chain form a network structure through a weak hydrogen bond to cause the mixture to gelate. That is, the Young's modulus of the mixture can be controlled by a ratio between the amounts of the first polysaccharide and the second polysaccharide, and the gelation does not occur when only one of the polysaccharides is present.

Via the foregoing gelation mechanism, the mixture may be suitably used particularly in the simulation of a low Young's modulus like that of an organ.

<Contents of First and Second Polysaccharides>

The respective blending amounts or respective contents of the first polysaccharide and the second polysaccharide in the hydrogel for forming the ultrasound phantom of this embodiment are each preferably 0.30 part by mass or more when the amount of the water is set to 94.00 parts by mass, and to obtain a uniform phantom free of any air bubble or the like, the contents are each preferably 0.30 part by mass or more and 3.00 parts by mass or less. The contents are each more preferably 0.30 part by mass or more and 1.00 part by mass or less, still more preferably 0.35 part by mass or more and 0.75 part by mass or less, still further more preferably 0.45 part by mass or more and 0.65 part by mass or less.

In addition, the total content of the first polysaccharide and the second polysaccharide in the hydrogel for forming the ultrasound phantom of this embodiment is preferably 0.60 part by mass or more and 3.00 parts by mass or less when the amount of the water is set to 94.00 parts by mass, and to obtain a uniform phantom free of any air bubble or the like, the total content is preferably 0.80 part by mass or more and 2.00 parts by mass or less. The total content is more preferably 0.60 part by mass or more and 1.50 parts by mass or less, still more preferably 1.00 part by mass or more and 1.20 parts by mass or less.

<Blending Weight Ratio Between First and Second Polysaccharides>

The blending mass ratio of the second polysaccharide with respect to the blending mass of the first polysaccharide in the hydrogel for forming the ultrasound phantom of this embodiment is preferably 0.33 or more and 3.00 or less, more preferably 0.50 or more and 2.00 or less, still more preferably 0.66 or more and 1.50 or less, still further more preferably 0.80 or more and 1.25 or less from the viewpoint of the ease with which the saccharides gelate.

<Method of Measuring Viscosity of Sol and its Thixotropy>

The viscosity of sol in this embodiment may be measured with a rotational viscometer. The viscosity was measured under the following conditions: under a temperature higher than the temperature at which the sol underwent a phase transition into a gel phase by 10° C., the measurement was performed at two rotational speeds, that is, 0.1 $sec^{-1}$ and 1.0 $sec^{-1}$.

The rotational viscometer that may be used is, for example, MCR302 dealt in by Anton Paar Japan K.K.

From the viewpoint of the dispersion stability of an ultrasonic scattering agent to be described later, the viscosity at a rotational speed of 0.1 $sec^{-1}$ is preferably 3 Pa·s or more and 300 Pa·s or less, more preferably 3 Pa·s or more and 100 Pa·s or less, and from the viewpoints of the dispersion stability of the ultrasonic scattering agent and the ease with which the ultrasound phantom is produced, the viscosity is still more preferably 5 Pa·s or more and 50 Pa·s or less.

From the viewpoint of the dispersion stability of the ultrasonic scattering agent to be described later, the viscosity at a rotational speed of 0.1 $sec^{-1}$ is preferably 3.0 or more times, more preferably 3.5 or more times, still more preferably 4.0 or more times as high as the viscosity at a rotational speed of 1.0 $sec^{-1}$.

<Container>

A container to be used in the ultrasound phantom of this embodiment is intended to hold the shape of the hydrogel of this embodiment. That is, the container in the ultrasound phantom of this embodiment is a container configured to store the hydrogel, the container having a holding portion, which is brought into contact with the hydrogel and is configured to hold the shape of the hydrogel. A material for the container is not particularly limited, and only needs to be a material that does not cause the deformation of the ultrasound phantom and the exudation of moisture. The shape of the container may be a cube, a rectangular parallelepiped, a columnar shape, or the like, or may be a shape imitating an organ. In addition, the inside of the container may be partially filled with a material except the hydrogel of this embodiment.

Further, a lid portion may be present at a position facing an acoustic coupling surface in the upper portion of the container for the purpose of preventing the evaporation of the moisture of the hydrogel. That is, the container in the ultrasound phantom of this embodiment may have a lid portion facing the acoustic coupling surface and a main body portion, which has the holding portion for holding the shape of the hydrogel and is fastened to the lid portion. A material for the lid portion is not particularly limited, and only needs to be a material that does not cause the exudation of moisture, and the shape of the material preferably has a structure to be brought into close contact with the holding portion or the main body portion.

<Acoustic Coupling Surface>

The hydrogel in the ultrasound phantom of this embodiment has an acoustic coupling surface to be acoustically coupled to an acoustic probe, and the container has the holding portion at a position different from that of the acoustic coupling surface. Further, the hydrogel in the ultrasound phantom of this embodiment has, at a position facing the acoustic coupling surface through the hydrogel, an acoustic wave-reducing portion configured to reduce the reflection of an acoustic wave from the acoustic coupling surface. The acoustic coupling surface in this embodiment refers to a surface to be acoustically coupled to the acoustic probe. The acoustic coupling surface is preferably a flat surface from the viewpoint of the transmissibility of an ultrasonic wave. In addition, the acoustic coupling surface may be the hydrogel of this embodiment, and may be covered with a material except the hydrogel of this embodiment. For example, the surface may be covered with a film-like material for the purpose of preventing the evaporation of the moisture of the hydrogel.

The phrase "acoustically coupled to the acoustic probe" as used herein means that the transmissibility of an ultrasonic wave is satisfactory. There is a large difference in acoustic impedance between the acoustic probe and a human body. Thus, an ultrasonic beam is reflected, and is hence not efficiently transmitted into the human body in some cases. Accordingly, a substance having an acoustic characteristic impedance intermediate between those of the acoustic probe and the human body needs to be inserted therebetween. The substance is the acoustic coupling surface, and the insertion of the acoustic coupling surface therebetween can minimize the reflection of the ultrasonic wave, and hence improves the transmissibility of the ultrasonic wave.

<Sound-Absorbing Material>

A sound-absorbing material in this embodiment refers to a material that attenuates an ultrasonic wave that has passed therethrough. That is, the sound-absorbing material is a material to be used in the acoustic wave-reducing portion. Thus, an ultrasonic wave that has entered from the acoustic coupling surface passes through the inside of the hydrogel, and then passes through the sound-absorbing material to be attenuated. As a result, a reflected wave from the container can be suppressed. Any material may be used for the sound-absorbing material as long as the material has a high transmission loss for an ultrasonic wave, and a rubber material is preferred, and a urethane rubber material is particularly preferred. The transmission loss is preferably as high as possible, and is preferably 15 $dB \cdot MHz^{-1} \cdot cm^{-1}$ or more, more preferably 20 $dB \cdot MHz^{-1} \cdot cm^{-1}$ or more, still more preferably 25 $dB \cdot MHz^{-1} \cdot cm^{-1}$ or more.

<Other Component>

Various components may be added as required as other components different from the first polysaccharide and the second polysaccharide to the ultrasound phantom of this embodiment.

<Sound Speed-Adjusting Agent>

A sound speed-adjusting agent may be added as any other component to the ultrasound phantom of this embodiment. Examples of the sound speed-adjusting agent include: inorganic compounds such as sodium hydrogen carbonate; organic compounds, such as urea, guanidine, a guanidine salt, glucose, and inositol; alcohols, such as ethanol, ethylene glycol, and glycerin; and organic solvents, such as N,N-dimethyl sulfoxide and N,N-dimethylformamide. In addition, the sound speed-adjusting agent is preferably water-soluble from the viewpoint of the transmittance of an ultrasonic wave. Further, to prevent a change in sound speed, a material that hardly volatilizes is preferred, and a material that does not decompose in water or a material that does not react with any other component is preferred.

The addition amount of the sound speed-adjusting agent is as follows: in the case of, for example, urea, when the mass of the water is set to 94.00 parts by mass, the addition amount of urea is preferably 2.00 parts by mass or more and 10.00 parts by mass or less, more preferably 4.00 parts by mass or more and 8.00 parts by mass or less, still more preferably 5.00 parts by mass or more and 7.00 parts by mass or less. In addition, a sound speed in an organ of a living organism is about 1,535 m/s, and hence the agent only needs to be added to the extent that the sound speed does not largely deviate from the value. For example, when an ultrasonic wave having a frequency of 3.5 MHz is passed through the ultrasound phantom, the sound speed of the ultrasonic wave is preferably 1,500 m/s or more and 1,600 m/s or less, more preferably 1,520 m/s or more and 1,550 m/s or less, still more preferably 1,530 m/s or more and 1,540 m/s or less.

<Ultrasonic Scattering Agent>

The ultrasound phantom of this embodiment may further include an ultrasonic scattering agent as any other component. An ultrasonic diagnostic apparatus performs image taking and measurement with a signal that has reached its detector out of ultrasonic waves scattered in the phantom. Accordingly, the addition of the ultrasonic scattering agent to a portion serving as a measurement object enables the image taking, and hence enables the measurement of the Young's modulus of the object.

In addition, the scattering efficiency of an ultrasonic wave is calculated by the acoustic impedance (=density×sound speed) of a substance scattering the wave. At a substance interface, the scattering efficiency becomes higher as a difference in acoustic impedance value between substances for forming the interface becomes larger.

A solid particle that may be used as the ultrasonic scattering agent is, for example, a known particle, such as an inorganic particle, a metal, a metal oxide, a carbon particle, or a spherical polymer. A material for the ultrasonic scattering agent is not particularly limited as long as the material is a solid having low water solubility. From the viewpoint of mechanical stability, for example, a carbon crystal particle, such as graphite or micro diamond, an amorphous carbon particle such as carbon black, a resin-made particle, such as a polyethylene particle, a polyethylene hollow sphere, or a polystyrene hollow sphere, an oxide fine particle, such as titanium oxide, alumina oxide, or silicon oxide, and a metal fine particle, such as tungsten, nickel, or molybdenum, are preferred. Of those, a carbon crystal particle is preferred particularly in consideration of its high acoustic impedance and its dispersibility in water.

The particle diameter of the ultrasonic scattering agent is determined in accordance with the wavelength of an ultrasonic wave to be input. The particle diameter of the ultrasonic scattering agent calculated from the wavelength of an ultrasonic wave emitted from the probe of an ultrasonic diagnostic apparatus is preferably 5 μm or more and 50 μm or less, more preferably 5 μm or more and 25 μm or less.

However, in general, a high-density particle having a particle diameter of 5 μm or more has a high sedimentation rate, and hence the particles of the ultrasonic scattering agent are separated during the gelation of the mixture of the first polysaccharide and the second polysaccharide from sol in some cases. Such sedimentation rate may be calculated from the following Stokes equation:

$$V = g(\rho_p - \rho_f)d_p^2/18\eta$$

where V represents the sedimentation rate (m/s), "g" represents a gravitational acceleration ($m/s^2$), $\rho_p$ represents the density ($kg/m^3$) of the particles, $\rho_f$ represents the density ($kg/m^3$) of a fluid, $d_p$ represents the diameter (m) of each of the particles, and $\eta$ represents the viscosity coefficient (Pa·s) of the fluid.

Accordingly, the sedimentation of the particles of the ultrasonic scattering agent can be prevented by reducing the particle diameter of the ultrasonic scattering agent, reducing a density difference between the ultrasonic scattering agent and the fluid, or increasing the viscosity coefficient of the fluid.

The content of the ultrasonic scattering agent only needs to be appropriately adjusted in accordance with a target scattering effect, and is hence not particularly limited. However, the content is preferably 0.50 part by mass or more and 20.00 parts by mass or less, more preferably 1.00 part by mass or more and 10.00 parts by mass or less, still more preferably 2.00 parts by mass or more and 7.00 parts by mass or less when the mass of the water is set to 94.00 parts by mass.

<Antiseptic>

The ultrasound phantom of this embodiment may include an antiseptic as any other component. In general, bacteria and fungi are liable to proliferate in the hydrogel, and hence the antiseptic is preferably used for suppressing the influences of the alteration of the hydrogel on its physical property values. Although the antiseptic that may be used is not particularly limited, an antiseptic having water solubility and a wide antimicrobial spectrum is preferred.

An antiseptic, a microbicidal agent, or an antimicrobial agent serving as a compound capable of suppressing the generation of bacteria and fungi is exemplified by alkyldiaminoethylglycine hydrochloride, sodium benzoate, ethanol, benzalkonium chloride, benzethonium chloride, chlorhexidine gluconate, chlorobutanol, sorbic acid, potassium sorbate, sodium dehydroacetate, methyl parahydroxybenzoate, ethyl parahydroxybenzoate, propyl parahydroxybenzoate, butyl parahydroxybenzoate, oxyquinoline sulfate, phenethyl alcohol, and benzyl alcohol.

Of those, a parahydroxybenzoic acid ester-based antiseptic is desired because the antiseptic has water solubility and a wide antimicrobial spectrum, and in particular, a small influence on a human body is desired. In addition, methyl parahydroxybenzoate is particularly preferred from the viewpoint of water solubility.

It is preferred that the antiseptic be appropriately added because its effect varies from compound to compound. In the case of, for example, methyl parahydroxybenzoate, when the mass of the water is set to 94.00 parts by mass, methyl parahydroxybenzoate only needs to be added in an amount of 0.10 part by mass or more and 0.30 part by mass or less, and the addition of an amount in the range exhibits a sufficient effect as an antiseptic.

<Antifoaming Agent>

The ultrasound phantom of this embodiment may include an antifoaming agent as any other component. The antifoaming agent is preferably used because the entry of air bubbles at the time of the production of the hydrogel excessively scatters an ultrasonic wave owing to a difference in acoustic impedance at a water-air interface. Examples of the antifoaming agent that may be used include: oils, such as a mineral oil, and oils and fats; surfactants, such as a fatty acid, a fatty acid ester, a phosphoric acid ester, and metal soap; and silicone compounds, such as a silicone oil and dimethylsiloxane. Of those, a silicone compound is particularly preferred because a small addition amount thereof exhibits a high antifoaming effect.

It is preferred that the antifoaming agent be appropriately added because its effect varies from compound to compound. In the case of, for example, the silicone compound, when the mass of the water is set to 94.000 parts by mass, the compound only needs to be added in an amount of 0.001 part by mass or more and 0.100 part by mass or less, and the addition of the compound in an amount in the range exhibits a sufficient effect as an antifoaming agent.

The ultrasound phantom of this embodiment preferably includes the water, the first polysaccharide, and the second polysaccharide, and the sound speed-adjusting agent, the ultrasonic scattering agent, the antiseptic, or the antifoaming agent serving as any other component. The total mass of those components is preferably 80 parts by mass or more and 100 parts by mass or less, more preferably 90 parts by mass or more and 100 parts by mass or less, still more preferably 95 parts by mass or more and 100 parts by mass or less when the mass of the entirety of the hydrogel is set to 100 parts by mass. The addition amount can sufficiently exhibit the function of this embodiment.

<Thickener>

The ultrasound phantom of this embodiment may include a thickener as any other component. The addition of the thickener can improve the dispersion stability of the ultrasonic scattering agent in sol. Examples of the thickener that may be used include: synthetic polymers, such as sodium polyacrylate and polyvinyl alcohol; and polysaccharides, such as a tamarind seed gum, a guar gum, a succinoglycan, and a diutan gum, and derivatives thereof, and cellulose derivatives. Meanwhile, such a thickener that its addition does not inhibit the solubility and gelation of the mixture of the first polysaccharide and the second polysaccharide is preferred.

<Gelling Agent>

The ultrasound phantom of this embodiment may include a gelling agent as any other component. The addition of the gelling agent can finely adjust the Young's modulus of the hydrogel. Examples of the gelling agent that may be used include: polysaccharides, such as agar, carrageenan, pectin, a gellan gum, sodium alginate, a tamarind seed gum, and curdlan; and gelatin.

The ultrasound phantom of this embodiment may include, for example, a colorant such as an aqueous dye or a pH adjuster such as a phosphate buffer as any other component.

A method of producing an ultrasound phantom according to this embodiment is characterized by including the steps of: producing a dispersion liquid by mixing water, a first polysaccharide containing a glucose residue in a main chain thereof, and a mannose residue and a glucuronic acid residue in a side chain thereof, a second polysaccharide containing a mannose residue in a main chain thereof and a galactose residue in a side chain thereof, and an ultrasonic scatterer; causing the dispersion liquid to solate by increasing a temperature thereof; and causing the dispersion liquid that has solated to gelate by reducing a temperature thereof.

A flowchart of the method of producing an ultrasound phantom of this embodiment is illustrated in FIG. 1. The method of producing an ultrasound phantom is not particularly limited. The water, the first polysaccharide, and the second polysaccharide, and as required, other components, such as a sound speed-adjusting agent, an ultrasonic scattering agent, an antiseptic, and an antifoaming agent, are mixed to produce a dispersion liquid. Then, the temperature of the dispersion liquid is increased to a temperature that is more than the first phase transition point (e.g., 80° C. or more and 90° C. or less) at which the first polysaccharide and the second polysaccharide therein are dissolved in the water. Thus, such sol that the first polysaccharide and the second polysaccharide are dissolved in the water is obtained. The liquid is stirred or heated as required until the distribution of the components incorporated thereinto becomes uniform.

Herein, the distribution of the components incorporated into the sol includes: an aspect in which the components are brought into equilibrium under the state of being dispersed in the solvent in a uniform manner macroscopically; and an aspect in which the components are brought into equilibrium under the state of being dissolved in the solvent in a uniform manner at a molecular level microscopically. The former includes the ultrasonic scattering agent and the antifoaming agent, and the latter includes the first polysaccharide, the second polysaccharide, the sound speed-adjusting agent, and the antiseptic.

The resultant sol is poured into a container having a desired shape, and is cooled to a temperature that is less than the second phase transition point at which the first polysaccharide and the second polysaccharide gelate. Thus, the ultrasound phantom can be obtained. A method for the cooling is not particularly limited, and the sol may be left at room temperature, or may be cooled with a desired medium such as water.

That is, the method of producing an ultrasound phantom preferably includes a step of cooling the sol, which contains the water, the first polysaccharide, and the second polysaccharide, and is in a state in which the dispersion liquid of the first polysaccharide and the second polysaccharide is dissolved in the water, to the temperature at which the first polysaccharide and the second polysaccharide gelate, to thereby provide the ultrasound phantom. Thus, an ultrasound phantom including a hydrogel containing the water, the first polysaccharide, and the second polysaccharide can be obtained.

Figure 2:
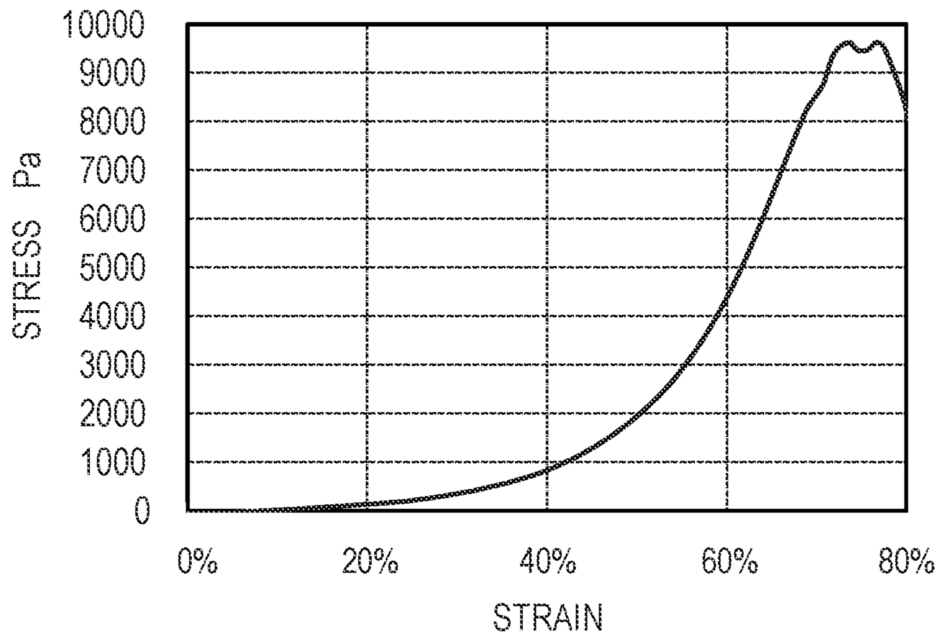
FIG. 2 is a graph for showing an example of the compressive strain-stress curve of a hydrogel.

Subsequently, the compression test of the resultant sol is performed to provide a compressive strain-stress curve, and information on whether or not the compressive stress of the sol monotonically increases at a compressive strain of 0% or more and 50% or less is obtained from the resultant compressive strain-stress curve. Thus, whether or not the hydrogel of this embodiment can be produced without any problem can be confirmed. The graph of the compressive strain-stress curve to be specifically obtained in this embodiment is shown in FIG. 2.

A sample for the compression test may be a sample cut out of the resultant sol, or may be separately produced by: pouring the resultant sol into a container equal in size to the sample for the compression test; and cooling the sol to a temperature (e.g., room temperature) that is less than the second phase transition point. That is, to obtain the compressive strain-stress curve, the production method of this embodiment may further include, during the step of causing the dispersion liquid to gelate, or after the step of causing the dispersion liquid to gelate, a step of obtaining a stress-strain curve by subjecting the dispersion liquid that has gelated to a compression test.

In, for example, an ultrasonic diagnostic apparatus such as ultrasonic elastography for calculating the accurate Young's modulus of an organ, the ultrasound phantom of this embodiment may be used as a phantom for ultrasonography in the calibration of the apparatus.

EXAMPLES

The present invention is described in detail below by way of Examples, but this embodiment is not limited to these Examples. In the following formulations, the term "part(s)" is by mass unless otherwise specified.

<Material>

Materials used in Examples 1 to 14 and Comparative Examples 1 to 7 are listed below.

[First Polysaccharide (A)]

Xanthan Gum 1 Product Name: KELZAN AP (CP Kelco U.S., Inc.)

A xanthan gum 1 has a main chain in which β-D-glucose residues are bonded to each other at their 1- and 4-positions through a glycosidic bond, and a side chain in which a β-D-mannose residue whose 4- and 6-positions are cross-linked to each other by pyruvic acid, a β-D-glucuronic acid residue, and an α-D-mannose residue whose 6-position is acetylated are bonded to each other in the stated order at their 1- and 4-positions, and 1- and 2-positions, respectively through glycosidic bonds, and the gum mainly has a structure in which the 1-position of the acetylated α-D-mannose residue in the side chain and the 4-position of the β-D-glucose residue in the main chain are bonded to each other through a glycosidic bond. The ratio of the number of the mannose residues in the side chain to the number of the glucose residues in the main chain is 1.0, and the ratio of the number of the glucuronic acid residues in the side chain to the number of the glucose residues in the main chain is 0.5.

Xanthan Gum 2 Product Name: KELZAN T (CP Kelco U.S., Inc.)

A xanthan gum 2 has a main chain in which β-D-glucose residues are bonded to each other at their 1- and 4-positions through a glycosidic bond, and a side chain in which a β-D-mannose residue whose 4- and 6-positions are cross-linked to each other by pyruvic acid, a β-D-glucuronic acid residue, and an α-D-mannose residue whose 6-position is acetylated are bonded to each other in the stated order at their 1- and 4-positions, and 1- and 2-positions, respectively through glycosidic bonds, and the gum mainly has a structure in which the 1-position of the acetylated α-D-mannose residue in the side chain and the 4-position of the β-D-glucose residue in the main chain are bonded to each other through a glycosidic bond. The ratio of the number of the mannose residues in the side chain to the number of the glucose residues in the main chain is 1.0, and the ratio of the number of the glucuronic acid residues in the side chain to the number of the glucose residues in the main chain is 0.5. The viscosity of a 1% aqueous solution of the gum is 1,100 mPa·s.

[Second Polysaccharide (B)]

Locust Bean Gum 1 (FUJIFILM Wako Pure Chemical Corporation)

A locust bean gum 1 has a main chain in which β-D-mannose residues are bonded to each other at their 1- and 4-positions through a glycosidic bond, and a side chain formed of an α-D-galactose residue, and the gum mainly has a structure in which the 1-position of the α-D-galactose residue in the side chain and the 6-position of the β-D-mannose residue in the main chain are bonded to each other through a glycosidic bond. The ratio of the number of the galactose residues in the side chain to the number of the mannose residues in the main chain is 0.25.

Tara Gum Product Name: TARA GUM a (Ina Food Industry Co., Ltd.)

A tara gum has a main chain in which β-D-mannose residues are bonded to each other at their 1- and 4-positions through a glycosidic bond, and a side chain formed of an α-D-galactose residue, and the gum has a structure in which the 1-position of the α-D-galactose residue in the side chain and the 6-position of the β-D-mannose residue in the main chain are bonded to each other through a glycosidic bond. The ratio of the number of the galactose residues in the side chain to the number of the mannose residues in the main chain is 0.33.

Locust Bean Gum 2 Product Name: GENU GUM RL-200Z (CP KELCO a Huber Company)

A locust bean gum 2 has a main chain in which β-D-mannose residues are bonded to each other at their 1- and 4-positions through a glycosidic bond, and a side chain formed of an α-D-galactose residue, and the gum mainly has a structure in which the 1-position of the α-D-galactose residue in the side chain and the 6-position of the β-D-mannose residue in the main chain are bonded to each other through a glycosidic bond. The ratio of the number of the galactose residues in the side chain to the number of the mannose residues in the main chain is 0.25. The viscosity of a 1% aqueous solution of the gum is 3,600 mPa·s.

Locust Bean Gum 3 Product Name: MEYPRO-LBG Fleur M-200 (Danisco Zaandam B.V.)

A locust bean gum 3 has a main chain in which β-D-mannose residues are bonded to each other at their 1- and 4-positions through a glycosidic bond, and a side chain formed of an α-D-galactose residue, and the gum mainly has a structure in which the 1-position of the α-D-galactose residue in the side chain and the 6-position of the β-D-mannose residue in the main chain are bonded to each other through a glycosidic bond. The ratio of the number of the galactose residues in the side chain to the number of the mannose residues in the main chain is 0.25. The viscosity of a 1% aqueous solution of the gum is 3,100 mPa·s.

[Other Components]

- Other polysaccharide: agar (Kishida Chemical Co., Ltd.)
- Sound speed-adjusting agent: urea (Kishida Chemical Co., Ltd.)
- Ultrasonic scattering agent: graphite, product name: NICABEADS (trademark) ICB-1020 (Nippon Carbon Co., Ltd.)
- Antiseptic: methyl parahydoxybenzoate (Kishida Chemical Co., Ltd.)
- Antifoaming agent: silicone-based antifoaming agent, product name: KS-530 (Shin-Etsu Chemical Co., Ltd.)

<Evaluation Method>

[Viscosity and Thixotropy]

Water, a first polysaccharide, and a second polysaccharide, and as required, other components, such as a sound speed-adjusting agent, an ultrasonic scattering agent, an antiseptic, and an antifoaming agent, were mixed to provide a dispersion liquid, and the dispersion liquid was heated and stirred at a temperature equal to or more than its solation temperature to be caused to completely solate. The viscosities of the sol were measured with the φ25 mm cone plate of a viscoelasticity-measuring apparatus (MCR302 manufactured by Anton Paar Japan K.K.) at a temperature of 70° C., and two kinds of rotational speeds, that is, 0.1 $sec^{-1}$ and 1.0 $sec^{-1}$.

When the viscosity at a rotational speed of 0.1 $sec^{-1}$ was 3.0 Pa·s or more and 300 Pa·s or less, the viscosity was evaluated as A. When the viscosity is 3.0 Pa·s or more, the sedimentation of the ultrasonic scatterer is suppressed during a time period from the cooling of the mixed liquid that has solated to its gelation, and when the viscosity is 300 Pa·s or less, the liquid can be uniformly stirred with a typical stirring apparatus. In addition, when the viscosity at a rotational speed of 0.1 $sec^{-1}$ was 3.0 or more times as high as the viscosity at a rotational speed of 1.0 $sec^{-1}$, the thixotropy of the liquid was evaluated as A. When the viscosity at a rotational speed of 0.1 $sec^{-1}$ is 3.0 or more times as high as the viscosity at a rotational speed of 1.0 $sec^{-1}$, the viscosity of the sol liquid of the mixture is reduced by a rotational shear force exhibited by the stirring blade of the apparatus, and hence the contents in the liquid can be uniformly mixed.

When the results of both the viscosity evaluation and the thixotropy evaluation described above are A, the sol liquid of the mixture is easily stirred, and hence a uniform sol liquid is obtained. In addition, when the sol liquid is cooled to be caused to gelate, the sedimentation rate of the particles of the ultrasonic scattering agent becomes negligibly low. Accordingly, it can be said that the physical properties are suitable for the production of an ultrasound phantom.

[Young's Modulus]

A hydrogel obtained by cooling the above-mentioned sol liquid was subjected to dynamic viscoelasticity measurement with a viscoelasticity-measuring apparatus (MCR302 manufactured by Anton Paar Japan K.K.) under the conditions of a strain of 1% and a frequency of 1 Hz, and the value of its storage modulus G' was determined. An ultrasound phantom having the following sample shape was used: a columnar shape having a diameter of 25 mm and a thickness of 7 mm. The Young's modulus E of the ultrasound phantom is calculated from the storage modulus G' by using its Poisson's ratio ν in accordance with the following equation. In addition, the Poisson's ratio ν was assumed to be 0.5 because a change in volume of the ultrasound phantom at the time of the measurement was small.

$$E = G' \times 2(1 + \nu)$$

When the Young's modulus was from 0.1 kPa to 5.0 kPa, the Young's modulus was evaluated as A.

[Compression Test]

The compressive strain-stress curve of the hydrogel obtained by cooling the above-mentioned sol liquid was measured with a universal tester (RTF-1250, A&D Company, Limited) under the conditions of a compression speed of 10 mm/min and a maximum compressive strain of 80%, and the compressive strain (%) at which the breakage of the hydrogel occurred was determined. The strain was defined as a compressive breaking strain. An ultrasound phantom having the following sample shape was used: a columnar shape having a diameter of 29 mm and a height of 12.5 mm.

The compressive breaking strain of the hydrogel was defined as the point at which the compressive stress thereof reduced when the compressive strain thereof was increased in increments of 0.5%. When the intervals at which the compressive strain was measured were less than 0.5%, the value closest to 0.5×n ("n" represented an integer of from 0 to 160) was adopted. In addition, when the compressive stress did not reduce even once until the compressive strain reached 80%, the compressive breaking strain was defined as 80% or more.

When the compressive breaking strain was 50% or more, the result of the compression test of the hydrogel was evaluated as A. When the compressive breaking strain is 50% or more, the strain can be measured without any breakage due to the pressing of a probe or the like against the hydrogel.

Examples 1 to 14 and Comparative Examples 1 to 7

<Method of Producing Ultrasound Phantom>

[Production Example]

The production procedure of Example 1 is described as an example of a production procedure for an ultrasound phantom. In each of the other examples, that is, Examples 2 to 14 and Comparative Examples 1 to 7, an ultrasound phantom was produced while only the kinds and amounts of materials were changed in accordance with a formulation shown in each of Table 1 to Table 3 without any change of the production procedure of Example 1.

An ultrasonic wave-absorbing tile (Aptflex F28 manufactured by Precision Acoustics Ltd., transmission loss: 30 $dB \cdot MHz^{-1} \cdot cm^{-1}$) cut into a size measuring 100 mm in width by 100 mm in depth by 10 mm in height was bonded to the bottom portion of a polypropylene-made container having internal dimensions measuring 120 mm in width by 120 mm in depth by 90 mm in height with a water-resistant double-sided tape.

1,504 Grams of tap water and 0.32 g of an antifoaming agent (KS-530) were loaded into a 2-liter separable flask, and a water bath and a stirring apparatus mounted with a stirring blade were set. A mixture obtained by sufficiently mixing 96 g of a sound speed-adjusting agent (urea), 64 g of an ultrasonic scatterer (NICABEADS (trademark) ICB1020), 3.2 g of an antiseptic (methyl parahydroxybenzoate), 4.8 g of a first polysaccharide (xanthan gum: KELZAN AP), and 4.8 g of a second polysaccharide (locust bean gum) was gradually loaded into the flask while the contents in the flask were stirred at 300 rpm. The resultant mixture was continuously stirred at 200 rpm for 16 hours while its temperature was kept at room temperature. Next, the temperature of the water bath was increased to 90° C., and the mixture was heated and stirred at 300 rpm for 4 hours to produce a sol liquid of the mixture.

The above-mentioned sol liquid of the mixture was poured into the above-mentioned polypropylene-made container having bonded thereto the ultrasound wave-absorbing tile up to a height distant from the upper end of the container by 1 cm, and was left at room temperature for 24 hours to produce an ultrasound phantom of Example 1. In addition, a viscosity evaluation and a thixotropy evaluation were performed by the above-mentioned evaluation methods through use of the above-mentioned sol liquid. Further, the above-mentioned sol liquid of the mixture was poured into each of molds having sample sizes for a compression test and for Young's modulus measurement, and was left at room temperature for 24 hours. Thus, test samples were produced.

A Young's modulus evaluation and a compression test evaluation were performed by the above-mentioned evaluation methods through use of the test samples.

The obtained results are shown in Table 1 to Table 3.

TABLE 1

| | Classification | Kind of material | Example 1 | Example 2 | Example 3 | Example 4 | Example 5 | Example 6 | Comparative Example 1 | Comparative Example 2 |
|---|---|---|---|---|---|---|---|---|---|---|
| Material formulation | Water | Tap water | 94.00 | 94.00 | 94.00 | 94.00 | 94.00 | 94.00 | 94.00 | 94.00 |
| | Sound speed-adjusting agent | Urea | 6.00 | 6.00 | 6.00 | 6.00 | 6.00 | 6.00 | 6.00 | 6.00 |
| | Ultrasonic scattering agent | NICABEADS (trademark) ICB1020 | 4.00 | 4.00 | 4.00 | 4.00 | 4.00 | 4.00 | 4.00 | 4.00 |
| | Antiseptic | Methyl parahydroxybenzoate | 0.20 | 0.20 | 0.20 | 0.20 | 0.20 | 0.20 | 0.20 | 0.20 |
| | Antifoaming agent | KS-530 | 0.02 | 0.02 | 0.02 | 0.02 | 0.02 | 0.02 | 0.02 | 0.02 |
| | First polysaccharide | Xanthan gum 1 | 0.30 | 0.50 | 1.00 | 1.50 | 0.50 | 1.00 | 0.20 | 2.00 |
| | Second polysaccharide | Tara gum | | | | | 0.75 | 1.50 | | |
| | | Locust bean gum 1 | 0.30 | 0.50 | 1.00 | 1.50 | | | 0.20 | 2.00 |
| Physical property of sol | Viscosity at 0.1 $sec^{-1}$ [Pa · s] | | 3.5 | 6.6 | 68.6 | 170.0 | 101.2 | 237.9 | 1.1 | 376.1 |
| | Viscosity evaluation | | A | A | A | A | A | A | C | C |
| | Viscosity at 0.1 $sec^{-1}$/ viscosity at 1.0 $sec^{-1}$ | | 3.6 | 4.8 | 5.5 | 5.9 | 5.2 | 5.5 | 3.5 | 6.3 |
| | Thixotropy evaluation | | A | A | A | A | A | A | A | A |
| Physical property of gel | Young's modulus [kPa] | | 0.22 | 0.66 | 1.73 | 3.10 | 0.78 | 2.45 | 0.13 | 5.45 |
| | Young's modulus evaluation | | A | A | A | A | A | A | A | C |
| | Compressive breaking strain [%] | | 69% | 80% or more | 61% | 58% | 65% | 62% | 59% | 58% |
| | Compression test evaluation | | A | A | A | A | A | A | A | A |

TABLE 2

| | Classification | Kind of material | Example 7 | Example 8 | Example 9 | Example 10 | Comparative Example 3 | Comparative Example 4 | Comparative Example 5 | Comparative Example 6 | Comparative Example 7 |
|---|---|---|---|---|---|---|---|---|---|---|---|
| Material formulation | Water | Tap water | 94.00 | 94.00 | 94.00 | 94.00 | 94.00 | 94.00 | 94.00 | 94.00 | 94.00 |
| | Sound speed-adjusting agent | Urea | 6.00 | 6.00 | 6.00 | 6.00 | 6.00 | 6.00 | 6.00 | 6.00 | 6.00 |
| | Ultrasonic scattering agent | NICABEADS (trademark) ICB1020 | 4.00 | 4.00 | 4.00 | 4.00 | 4.00 | 4.00 | 4.00 | 4.00 | 4.00 |
| | Antiseptic | Methyl parahydroxybenzoate | 0.20 | 0.20 | 0.20 | 0.20 | 0.20 | 0.20 | 0.20 | 0.20 | 0.20 |
| | Antifoaming agent | KS-530 | 0.02 | 0.02 | 0.02 | 0.02 | 0.02 | 0.02 | 0.02 | 0.02 | 0.02 |
| | First polysaccharide | Xanthan gum 1 | 0.25 | 0.33 | 0.67 | 0.75 | 0.20 | 0.50 | | 0.50 | |
| | Second polysaccharide | Locust bean gum 1 | 0.75 | 0.67 | 0.33 | 0.25 | 0.80 | | 0.50 | | 0.50 |
| | Other polysaccharide | Agar | | | | | | | | 0.25 | 0.25 |
| Physical property of sol | Viscosity at 0.1 $sec^{-1}$ [Pa · s] | | 5.9 | 8.1 | 19.6 | 31.2 | 4.8 | 4.1 | 2.1 | 4.3 | 2.4 |
| | Viscosity evaluation | | A | A | A | A | A | A | C | A | C |
| | Viscosity at 0.1 $sec^{-1}$/viscosity at 1.0 $sec^{-1}$ | | 3.1 | 4.3 | 3.9 | 4.8 | 2.4 | 3.0 | 2.4 | 3.1 | 2.4 |
| | Thixotropy evaluation | | A | A | A | A | C | A | C | A | C |
| Physical property of gel | Young's modulus [kPa] | | 0.30 | 0.40 | 0.53 | 0.54 | 0.21 | — | — | 2.80 | 2.90 |
| | Young's modulus evaluation | | A | A | A | A | A | C | C | A | A |
| | Compressive breaking strain [%] | | 69% | 72% | 72% | 68% | 48% | — | — | 21% | 23% |
| | Compression test evaluation | | A | A | A | A | C | C | C | C | C |

TABLE 3

| | Classification | Kind of material | Example 11 | Example 12 | Example 13 | Example 14 |
|---|---|---|---|---|---|---|
| Material formulation | Water | Tap water | 94.00 | 94.00 | 94.00 | 94.00 |
| | Sound speed-adjusting agent | Urea | 6.00 | 6.00 | 6.00 | 6.00 |
| | Ultrasonic scatterer | NICABEADS (trademark) ICB1020 | 4.00 | 4.00 | 4.00 | 4.00 |
| | Antiseptic | Methyl parahydroxybenzoate | 0.20 | 0.20 | 0.20 | 0.20 |
| | First polysaccharide | Xanthan gum 1 | 0.50 | 0.50 | 0.50 | |
| | | Xanthan gum 2 | | | | 0.50 |
| | Second polysaccharide | Locust bean gum 1 | 0.50 | | | |
| | | Locust bean gum 2 | | 0.50 | | |
| | | Locust bean gum 3 | | | 0.50 | |
| Physical property of sol | Viscosity at 0.1 $sec^{-1}$ [Pa · s] | | 6.6 | 10.3 | 9.9 | 6.7 |
| | Viscosity evaluation | | A | A | A | A |
| | Viscosity at 0.1 $sec^{-1}$/viscosity at 1.0 $sec^{-1}$ | | 4.8 | 5.3 | 5.2 | 4.9 |
| | Thixotropy evaluation | | A | A | A | A |
| Physical property of gel | Young's modulus [kPa] | | 0.67 | 1.32 | 1.21 | 0.69 |
| | Young's modulus evaluation | | A | A | A | A |
| | Compressive breaking strain [%] | | 80% or more | 80% or more | 80% or more | 80% or more |
| | Compression test evaluation | | A | A | A | A |

In Table 1 to Table 3, the numerical values of the respective materials each represent the number of parts by mass.

As can be seen from the results of Table 1 to Table 3, in each of Examples 1 to 14 according to this embodiment, the Young's modulus fell within the range of from 0.1 kPa to 5.0 kPa, and the compressive breaking strain was 50% or more. That is, it was able to be confirmed that the ultrasound phantom of this embodiment was resistant to a compressive strain despite having a low Young's modulus. In addition, in each of Examples 1 to 14 according to this embodiment, the viscosity at a rotational speed of 0.1 $sec^{-1}$ was 3.0 Pa·s or more, and the ratio of the viscosity at a rotational speed of 0.1 $sec^{-1}$ to the viscosity at a rotational speed of 1.0 $sec^{-1}$ was 3.0 or more. That is, it was able to be confirmed from the results of Examples 1 to 14 that at the time of the production of the ultrasound phantom of this embodiment, the mixture was able to be uniformly stirred, and during a time period from the cooling of the sol liquid of the uniform mixture to its gelation, the ultrasonic scattering agent and the like were able to be kept uniform without their sedimentation.

In the results of Table 1, in Comparative Example 1 in which the amounts of the first polysaccharide and the second polysaccharide were each 0.2 part by mass, the viscosity of the sol liquid was lower than 3.0 Pa·s, and hence the viscosity evaluation criterion was not satisfied. Meanwhile, in Comparative Example 2 in which the amounts of the first polysaccharide and the second polysaccharide were each 2.0 parts by mass, the viscosity of the sol liquid was higher than 300 Pa·s, and hence the viscosity evaluation criterion was not satisfied. Further, it was found that in Comparative Example 2, the Young's modulus was more than 5.0 kPa, and hence the Young's modulus evaluation criterion was also not satisfied. It was able to be confirmed from the foregoing that the following hydrogel was preferred as an ultrasound phantom: with respect to 94 parts by mass of its water, the amount of the first polysaccharide was 0.3 part by mass or more and 3.0 parts by mass or less, the amount of the second polysaccharide was 0.3 part by mass or more and 3.0 parts by mass or less, and the total of the first polysaccharide and the second polysaccharide was 0.6 part by mass or more and 3.0 parts by mass or less.

In the results of Table 2, in Comparative Example 3 in which the weight ratio of the second polysaccharide to the first polysaccharide was 0.25, the compression test evaluation criterion could not be satisfied. In addition, in Comparative Example 3, the ratio of the viscosity at a rotational speed of 0.1 $sec^{-1}$ to the viscosity at a rotational speed of 1.0 $sec^{-1}$ was less than 3.0. It was able to be confirmed from the foregoing that the weight ratio of the second polysaccharide to the first polysaccharide was preferably 0.33 or more.

In the results of Table 2, in each of Comparative Example 4 and Comparative Example 5 in which only one of the first polysaccharide or the second polysaccharide was incorporated, no gelation occurred, and hence no hydrogel could be obtained. In addition, in each of Comparative Example 6 and Comparative Example 7 in which only one of the first polysaccharide or the second polysaccharide was incorporated, but another polysaccharide that gelated was added, the resultant gel did not satisfy the compression test evaluation criterion. It was able to be confirmed from the foregoing that a hydrogel obtained by combining the first polysaccharide and the second polysaccharide was preferred as an ultrasound phantom.

The present disclosure provides the following ultrasound phantom and the method of producing the ultrasound phantom: the low Young's modulus of the phantom can be controlled, and the phantom is resistant to a compressive strain, and hence can be repeatedly used.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2023-036754, filed Mar. 9, 2023, and Japanese Patent Application No. 2024-009744, filed Jan. 25, 2024, which are hereby incorporated by reference herein in their entirety.

What is claimed is:

1. An ultrasound phantom comprising a hydrogel,
wherein the hydrogel contains:
water,
a first polysaccharide containing a glucose residue in a main chain thereof, and a mannose residue and a glucuronic acid residue in a side chain thereof, and
a second polysaccharide containing a mannose residue in a main chain thereof and a galactose residue in a side chain thereof,
wherein the hydrogel has a Young's modulus of 0.1 kPa to 5.0 kPa, and
wherein the hydrogel contains 0.3 part by mass or more of the first polysaccharide and 0.3 part by mass or more of the second polysaccharide with respect to 94 parts by mass of the water, and a total of the first polysaccharide and the second polysaccharide is 0.6 part by mass to 3.0 parts by mass.

2. The ultrasound phantom according to claim 1, wherein when the ultrasound phantom is compressed, a compressive stress thereof monotonically increases at a compressive strain of 0% to 50%.

3. The ultrasound phantom according to claim 1, wherein the first polysaccharide has a ratio of a number of mannose residues to a number of glucose residues of 0.8 to 1.2, and a ratio of a number of glucuronic acid residues to a number of glucose residues of 0.4 to 0.6.

4. The ultrasound phantom according to claim 1, wherein the second polysaccharide has a ratio of a number of galactose residues to a number of mannose residues of 0.2 to 0.4.

5. The ultrasound phantom according to claim 4, wherein the second polysaccharide has the ratio of the number of the galactose residues to the number of the mannose residues of 0.2 to 0.3.

6. The ultrasound phantom according to claim 1, wherein the hydrogel has a mass ratio of the second polysaccharide to the first polysaccharide of 0.33 to 3.00.

7. The ultrasound phantom according to claim 1, wherein when a viscosity of a sol liquid of a mixture obtained by increasing a temperature of the hydrogel to a temperature equal to or more than a solation temperature is measured with a rotational viscometer at 70°C, a viscosity thereof at a rotational speed of 0.1 $sec^{31\ 1}$ is 3 Pa·s to 300 Pa·s, and the viscosity at the rotational speed of 0.1 $sec^{-1}$ is 3.0 or more times as high as a viscosity thereof at a rotational speed of 1.0 $sec^{-1}$.

8. An ultrasound phantom comprising a hydrogel,
wherein the hydrogel contains:
water,
a first polysaccharide containing a glucose residue in a main chain thereof, and a mannose residue and a glucuronic acid residue in a side chain thereof, and
a second polysaccharide containing a mannose residue in a main chain thereof and a galactose residue in a side chain thereof,
wherein the hydrogel has a Young's modulus of 0.1 kPa to 5.0 kPa, and
wherein when a viscosity of a sol liquid of a mixture obtained by increasing a temperature of the hydrogel to a temperature equal to or more than a solation temperature is measured with a rotational viscometer at 70°C, a viscosity thereof at a rotational speed of 0.1 $sec^{-1}$ is 3 Pa·s to 300 Pa·s, and the viscosity at the rotational speed of 0.1 $sec^{-1}$ is 3.0 or more times as high as a viscosity thereof at a rotational speed of 1.0 $sec^{-1}$.

9. The ultrasound phantom according to claim 8, wherein when the ultrasound phantom is compressed, a compressive stress thereof monotonically increases at a compressive strain of 0% to 50%.

10. The ultrasound phantom according to claim 8, wherein the first polysaccharide has a ratio of a number of mannose residues to a number of glucose residues of 0.8 to 1.2, and a ratio of a number of glucuronic acid residues to a number of glucose residues of 0.4 to 0.6.

11. The ultrasound phantom according to claim 8, wherein the second polysaccharide has a ratio of a number of galactose residues to a number of mannose residues of 0.2 to 0.4.

12. The ultrasound phantom according to claim 11, wherein the second polysaccharide has the ratio of the number of the galactose residues to the number of the mannose residues of 0.2 to 0.3.

13. The ultrasound phantom according to claim 8, wherein the hydrogel has a mass ratio of the second polysaccharide to the first polysaccharide of 0.33 to 3.00.

* * * * *